US006455595B1

(12) United States Patent
O'Rear et al.

(10) Patent No.: US 6,455,595 B1
(45) Date of Patent: *Sep. 24, 2002

(54) METHODS FOR OPTIMIZING FISCHER-TROPSCH SYNTHESIS

(75) Inventors: Dennis J. O'Rear, Petaluma; Charles L. Kibby, Benicia; Georgieanna L. Scheuerman, Moraga, all of CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/621,904

(22) Filed: Jul. 24, 2000

(51) Int. Cl.$^7$ .......................... C07C 27/00; C07C 5/22; C12Q 1/00; C10L 1/04; C10G 71/00
(52) U.S. Cl. ....................... 518/700; 518/715; 585/671; 435/4; 208/15; 208/18
(58) Field of Search ................ 518/700, 715; 585/671; 435/4; 208/15, 18

(56) References Cited

U.S. PATENT DOCUMENTS

| | | | |
|---|---|---|---|
| 2,662,090 A | 12/1953 | Scharmann | 260/449.6 |
| 2,686,195 A | 8/1954 | McAdams et al. | 260/449.6 |
| 2,735,862 A | 2/1956 | Buchmann et al. | 260/449.6 |
| 2,850,515 A | 9/1958 | Riblett et al. | 260/449.6 |
| 2,882,244 A | 4/1959 | Milton | 252/455 |
| 3,130,007 A | 4/1964 | Breck | 23/113 |
| 3,216,789 A | 11/1965 | Breck | 23/113 |
| 3,415,736 A | 12/1968 | Ciric | 252/455 |
| 3,546,102 A | 12/1970 | Bertolacini | 208/138 |
| 3,574,092 A | 4/1971 | Mitsche | 208/139 |
| 3,679,575 A | 7/1972 | Bertolacini | 208/65 |
| 3,692,470 A | 9/1972 | Ciric | 423/328 |
| 3,702,886 A | 11/1972 | Argauer et al. | 423/328 |
| 3,709,979 A | 1/1973 | Chu | 423/328 |
| 3,832,449 A | 8/1974 | Rosinski et al. | 423/328 |
| RE28,341 E | 2/1975 | Wadlinger et al. | 208/120 |
| 3,972,983 A | 8/1976 | Ciric | 423/328 |
| 4,016,245 A | 4/1977 | Plank et al. | 423/328 |
| 4,018,711 A | 4/1977 | Bertolacini | 252/455 Z |
| 4,039,302 A | 8/1977 | Khera | 48/197 |
| 4,042,614 A | 8/1977 | Vannice et al. | 260/449 |
| 4,076,842 A | 2/1978 | Plank et al. | 423/328 |
| 4,077,995 A | 3/1978 | Khera | 260/449.6 |
| 4,086,262 A | 4/1978 | Chang et al. | 260/449.6 |
| 4,088,671 A | 5/1978 | Kobylinski | 260/449.6 |
| 4,104,320 A | 8/1978 | Bernard et al. | 260/673.5 |
| RE29,948 E | 3/1979 | Dwyer | 208/110 |
| 4,151,190 A | 4/1979 | Murchison et al. | 260/449 R |
| 4,171,320 A | 10/1979 | Vannice et al. | 260/449 R |
| 4,206,134 A | 6/1980 | Kugler et al. | 260/449 R |
| 4,241,036 A | 12/1980 | Flanigen et al. | 423/328 |
| 4,294,725 A | 10/1981 | Fraenkel et al. | 252/455 Z |
| 4,347,121 A | 8/1982 | Mayer et al. | 208/58 |
| 4,347,394 A | 8/1982 | Detz et al. | 585/419 |
| 4,370,224 A | 1/1983 | Eberly, Jr. et al. | 208/139 |
| 4,417,083 A | 11/1983 | Bernard et al. | 585/419 |
| 4,434,311 A | 2/1984 | Buss et al. | 585/444 |
| 4,447,316 A | 5/1984 | Buss et al. | 208/138 |
| 4,507,517 A | 3/1985 | Devries et al. | 585/415 |
| 4,523,047 A | 6/1985 | Chester et al. | |
| 4,534,853 A | 8/1985 | Long et al. | 208/120 |
| 4,544,674 A | 10/1985 | Fiato et al. | 518/717 |
| 4,552,731 A | 11/1985 | Vaughan | 423/118 |
| 4,556,477 A | 12/1985 | Dwyer | 208/111 |
| 4,579,986 A | 4/1986 | Sie | 585/324 |
| 4,585,747 A | 4/1986 | Valyocsik | 502/62 |
| 4,599,474 A | 7/1986 | Devries et al. | 585/415 |
| 4,624,968 A | 11/1986 | Kim et al. | 518/707 |
| 4,704,487 A | 11/1987 | Devries et al. | 484/417 |
| 4,704,493 A | 11/1987 | Devries et al. | 585/415 |
| 4,709,108 A | 11/1987 | Devries et al. | 585/415 |
| 4,734,537 A | 3/1988 | Devries et al. | 585/415 |
| 4,810,357 A | 3/1989 | Chester et al. | 208/78 |
| 4,814,533 A | 3/1989 | Devries et al. | 585/407 |
| 4,814,534 A | 3/1989 | Devries et al. | 585/407 |
| 4,814,538 A | 3/1989 | Devries et al. | 585/500 |
| 4,826,667 A | 5/1989 | Zones et al. | 423/277 |
| 4,834,958 A | 5/1989 | Zones | 423/277 |

(List continued on next page.)

FOREIGN PATENT DOCUMENTS

| | | |
|---|---|---|
| EP | 353915 | 7/1989 |
| GB | 1117568 | 11/1966 |
| GB | 2050859 A | 5/1980 |

OTHER PUBLICATIONS

Amelse, J.A., et al., "Iron Alloy Fischer–Tropsch Catalysts; III. Conversion Dependence of Selectivity and Water–Gas Shift," *J. Catalysis*, No. 72(1):95–110 (1981).

Courty, P., and Delmon, B., "Chimie Minérale.—Obtention d'oxydes mixtes divisés par décomposition de précurseurs amorphes (sels organiques amorphes)," *C.R. Acad. Sc. Paris*, p. 268 (May 28, 1969).

(List continued on next page.)

*Primary Examiner*—Jafar Parsa
(74) *Attorney, Agent, or Firm*—Burns, Doane, Swecker & Mathis, L.L.P.

(57) ABSTRACT

Methods for discovering optimum catalyst systems for the conversion of syngas to higher molecular weight products via Fischer-Tropsch synthesis are disclosed. A combinatorial approach is used to identify combinations of catalyst systems useful for performing the reactions. The combinations of catalyst systems include Fischer-Tropsch catalysts and olefin isomerization catalysts. The method can advantageously be used to generate a database of combinations of catalyst systems and/or reaction conditions that provide various product streams, such that as market conditions vary and/or product requirements change, conditions suitable for forming desired products can be identified with little or no downtime. The catalysts are combined in a logical manner, for example in the form of arrays. The combinations of catalysts can be evaluated using varied reaction conditions, which can provide a) a combinatorial library of product streams and a database including the combination of catalysts and reaction conditions to provide each product stream and/or b) the optimum combination of catalysts and reaction conditions for obtaining a desired product stream.

16 Claims, No Drawings

U.S. PATENT DOCUMENTS

| | | | | |
|---|---|---|---|---|
| 4,859,442 A | 8/1989 | Zones et al. | ................ | 423/277 |
| 4,910,006 A | 3/1990 | Zones | ........................ | 423/328 |
| 4,963,337 A | 10/1990 | Zones | ........................ | 423/277 |
| 5,053,373 A | 10/1991 | Zones | ........................ | 502/64 |
| 5,106,801 A | 4/1992 | Zones | ........................ | 502/64 |
| 5,162,284 A | 11/1992 | Soled et al. | ................ | 502/324 |
| 5,177,281 A | 1/1993 | Haag et al. | ................ | 585/324 |
| 5,200,377 A | 4/1993 | Zones et al. | ................ | 502/62 |
| 5,202,014 A | 4/1993 | Zones et al. | ................... | 208/46 |
| 5,237,120 A | 8/1993 | Haag et al. | ................ | 585/666 |
| 5,254,514 A | 10/1993 | Nakagawa | .................. | 502/62 |
| 5,316,753 A | 5/1994 | Nakagawa | ................. | 423/706 |
| 5,321,194 A | 6/1994 | Apelian et al. | ............. | 585/671 |
| 5,348,982 A | 9/1994 | Herbolzheimer et al. | ... | 518/700 |
| 5,362,378 A | 11/1994 | Borghard et al. | | |
| 5,437,855 A | 8/1995 | Valyocsik | ................... | 423/706 |
| 5,523,510 A | 6/1996 | Pellet et al. | ................ | 585/671 |
| 5,559,068 A | 9/1996 | Chen et al. | ................. | 502/213 |
| 5,580,540 A | 12/1996 | Nakagawa | ................. | 423/718 |
| 5,591,421 A | 1/1997 | Zones | ........................ | 423/706 |
| 5,624,657 A | 4/1997 | Vaughan | .................... | 423/700 |
| 5,689,031 A * | 11/1997 | Berlowwitz et al. | ........ | 585/734 |
| 5,840,485 A * | 11/1998 | Lebl | ............... | 435/6 |
| 5,849,975 A | 12/1998 | Kluksdahl et al. | .......... | 585/671 |
| 5,980,839 A | 11/1999 | Bier et al. | .................. | 422/209 |
| 5,985,238 A | 11/1999 | Pasquale et al. | ............ | 423/706 |
| 6,001,311 A | 12/1999 | Brennan | ..................... | 422/131 |
| 6,004,617 A * | 12/1999 | Schultz | .......................... | 427/8 |
| 6,030,917 A | 2/2000 | Weinberg et al. | ........... | 502/104 |
| 6,036,923 A | 3/2000 | Laugharn, Jr. et al. | .. | 422/82.13 |

OTHER PUBLICATIONS

Deckwer, W.–D., et al., "Modeling the Fischer–Tropsch Synthesis in the Slurry Phase," *Ing. Eng. Chem. Process Des. Dev.*, 21(2):231–241 (1982).

Gmelins Handbuch der Anorganische Chemie 8, Auflage (1959), p. 5 *.

Hu, Y.C., "Unconventional olefin processes," *Hydrocarbon Processing*, May 1983, 88–96.

Khan, M.K.Z., et al., *AICHE 1981 Summer Nat'l Meeting Preprint No 408*, "The Synthesis of Light Hydrocarbons from CO and $H_2$ Mixtures over Selected Metal Catalysts," ACS $173^{rd}$ Symposium, Fuel Division, New Orleans (Mar. 1977).

Kitzelmann, D., et al., "Zur selektiven Hydrierung von Kohlenmonoxid zu $C_2$–bis $C_4$–Olefinen," *Chem. Ing. Tech.*, 49(6):463–468 (1977).

Köbel et al., "The Fischer–Tropsch Synthesis in the Liquid Phase," *Catal. Rev.–Sci. Eng.*, 21(n):225–274 (1980).

Lo, C., et al., "Mössbauer and Magnetic Studies of Bifunctional Medium–Pore Zeolite–Iron Catalysts Used in Synthesis Gas Conversion," *Adv. Chem. Ser.*, 194:573–88 (1981).

Nakamura, M., et al., "Fischer–Tropsch Synthesis with Iron–Cobalt Alloy Catalysts," *Stud. Surf. Sci. Catal.*, 7(pt.A):432–446 (1981).

Ramachandran et al., *Bubble Column Slurry Reactor*, "Three–Phase Catalytic Reactors," 10:308–332, Gordon and Broch Science Pub. (1983).

Shah, Y.T., et al., "Design Parameters Estimations for Bubble Column Reactors," *AIChE Journal*, 28(3):353–379 (May 1982).

Stanfield, R.M., et al., "Mössbauer Spectroscopy of Supported Fe–Co Alloy Catalysts for Fischer–Tropsch Synthesis," *J. Catalysis*, No. 72(1):37–50 (1981).

Van der Woude, F., et al., "Mössbauer Effect in Iron and Dilute Iron Alloys," *Physics Reports* (*Section C of Physics Letters*), 12(5):335–374 (1974).

Xu et al., "Don't rule out iron catalysts for Fischer–Tropsch synthesis," *Chemtech*, Jan 1998, pp. 47–53.

* cited by examiner

METHODS FOR OPTIMIZING FISCHER-TROPSCH SYNTHESIS

FIELD OF THE INVENTION

This invention is generally in the area of combinatorial chemistry, in particular the use of combinatorial chemistry to optimize Fischer-Tropsch synthesis, primarily to form hydrocarbons in the distillate fuel and/or lube base oil ranges.

BACKGROUND OF THE INVENTION

The majority of fuel today is derived from crude oil. Crude oil is in limited supply, and fuel derived from crude oil tends to include nitrogen-containing compounds and sulfur-containing compounds, which are believed to cause environmental problems such as acid rain.

Although natural gas includes some nitrogen- and sulfur-containing compounds, methane can be readily isolated in relatively pure form from natural gas using known techniques. Many processes have been developed that can produce fuel compositions from methane. Most of these processes involve the initial conversion of methane to synthesis gas ("syngas").

Fischer-Tropsch chemistry is typically used to convert the syngas to a product stream that includes combustible fuel, among other products. A limitation associated with Fischer-Tropsch chemistry is that it tends to produce a broad spectrum of products, ranging from methane to wax. Product slates for syngas conversion over Fischer-Tropsch catalysts (Fe, Co and Ru) are controlled by polymerization kinetics with fairly constant chain growth probabilities, that fix the possible product distributions. Heavy products with a relatively high selectivity for wax are produced when chain growth probabilities are high. Methane is produced with high selectivity when chain growth probabilities are low.

Methane can be recirculated to ultimately yield combustible liquid fuel. Wax can be processed, for example by hydrocracking and/or hydrotreating followed by oligomerization, to yield combustible liquid fuel. However, it would be advantageous to have new methods for providing a product stream from a Fischer-Tropsch process that has a higher proportion of combustible liquid fuel with less methane to recirculate and/or less wax to process.

Traditional Fischer-Tropsch synthesis has been modified by incorporating an acidic component, such as a zeolite, into the catalyst bed. When $C_4+$ alpha-olefins are produced, the alpha-olefins isomerize to more substituted olefins, cyclize to form aromatics, and/or heavier products are hydrocracked in the presence of the acid catalyst. This reduces the chain growth probability for $C_4+$ and largely minimizes wax formation.

For example, U.S. Pat. No. 4,086,262 to Chang et al. teaches conducting Fischer-Tropsch synthesis with ZSM-5 intimately mixed with the Fischer-Tropsch catalyst. Chang focused on obtaining high octane gasoline (i.e., highly branched hydrocarbons in the gasoline range).

Most work since then has focused on improving the catalyst components and continues to provide highly branched hydrocarbons in the high octane gasoline range. The catalysts are typically iron catalysts, since they operate at higher temperatures where the zeolites tend to be more active. In addition to intimate mixtures of zeolites and Fischer-Tropsch catalysts, some carbon monoxide hydrogenation components have been incorporated directly on zeolites (see, for example, U.S. Pat. No. 4,294,725).

There is a growing interest in developing "greener" diesel fuels, i.e., fuels which do not contain aromatic, nitrogen or sulfur compounds. Straight chain or slightly branched paraffins in the diesel fuel range tend to have relatively high cetane values. Ideally, such fuels could be provided directly from Fischer-Tropsch reactors if the right combinations of Fischer-Tropsch catalysts and zeolites could be found. However, known combinations of zeolites and Fischer-Tropsch catalysts to date have provided mainly highly branched paraffins in the gasoline range.

It would be advantageous to provide methods for discovering optimum catalyst systems for converting syngas to higher molecular weight products, for example hydrocarbons in the distillate fuel and/or lube base stock base oil ranges. The present invention provides such methods.

SUMMARY OF THE INVENTION

The present invention is directed to methods for optimizing the conversion of syngas to hydrocarbons via Fischer-Tropsch synthesis, preferably to form hydrocarbons in the distillate fuel and/or lube base oil ranges. The methods use a combinatorial approach to identify combinations of catalyst systems useful for performing the Fischer-Tropsch reactions. The catalyst combinations include both a Fischer-Tropsch catalyst and a relatively acidic catalyst, for example a molecular sieve, for isomerizing double bonds in $C_4+$ olefins as they are formed. The methods can advantageously be used to generate a database of combinations of catalyst systems and, optionally, reaction conditions, that provide various product streams. As market conditions vary and/or product requirements change, conditions suitable for forming desired products can be identified with little or no downtime using the methods described herein.

Libraries of catalysts suitable for use in a first catalyst system (Fischer-Tropsch catalysts) and a second catalyst system (olefin isomerization catalysts) are prepared. The libraries can optionally include catalysts that possess both types of activity, namely, that can convert syngas to olefins and also that isomerize the olefins.

The catalysts are preferably combined in a logical manner, for example in an A×B array, where each position in the A column includes one or more catalysts from the first catalyst system, and each position in the B row includes one or more catalysts from the second catalyst system. In this manner, virtually every possible combination of catalysts in the libraries can be evaluated. The combinations of catalysts can be evaluated using varied reaction conditions, which can provide a) a combinatorial library of product streams and a database including the combination of catalysts and reaction conditions to provide each product stream and/or b) the optimum combination of catalysts and reaction conditions for obtaining a desired product stream.

In addition to catalyst composition and reaction conditions, a third set of variables with great influence on the catalytic activity/selectivity is the manner in which various "pre-treatment" steps are carried out. Such pre-treatment variations include the time and temperature of catalyst washing; heating rate, hold time, hold temperature, and relative humidity during drying. The same pre-treatments can be varied during catalyst calcining, reduction, and activation. In catalyst reduction, the hydrogen content and total pressure can also be varied, as can the pressure and CO partial pressure during activation in CO. Other reduction methods can also be used, including as treatment with citrate, alcohols, and metal hydrides. Additional pre-treatments can also be performed, including modifying the acidity using acid leaching, base titration, ion exchange, vapor deposition of Si or Al species and steaming. These pre-treatments can be done individually or in combination on the individual catalyst components or on the composite. These different pre-treatments can be used with the different catalyst compositions to increase the size of the catalyst libraries. Alternatively, a single catalyst can be subjected to a plurality of different pre-treatments, or a library of catalysts can be subjected to a single pre-treatment, with the process repeated as desired.

The products can include olefins such as ethylene, iso-paraffins, and combinations thereof, and preferably include iso-paraffins in the distillate fuel and/or lube base stock ranges, and, more preferably, iso-paraffins in the jet or diesel range.

DETAILED DESCRIPTION OF THE INVENTION

The present invention is directed to methods for optimizing the conversion of syngas to hydrocarbons via Fischer-Tropsch synthesis, preferably forming hydrocarbons in the distillate fuel and/or lube base oil ranges. The methods use a combinatorial approach to identify combinations of catalyst systems useful for performing the Fischer-Tropsch reactions.

The catalyst combinations include a first catalyst system (a Fischer-Tropsch catalyst) and a second catalyst system (an olefin isomerization catalyst), where the catalysts are preferably defined both by composition and the manner in which they are pre-treated, individually or together. The combinations can be laid out in a logical fashion, for example in arrays. Where different classes of Fischer-Tropsch catalysts are used, for example catalysts with low chain growth probabilities and catalysts with high chain growth probabilities, they can advantageously be placed in sub-arrays where the entire array includes all of the above catalysts. The arrays can be ordered in such a fashion as to expedite synthesis and/or evaluation, to maximize the informational content obtained from the testing and to facilitate the rapid evaluation of that data. The reactions are preferably carried out in a reaction vessel capable of performing a plurality of simultaneous or substantially simultaneous reactions that involve gaseous reagents, solid phase catalysts and relatively high temperatures and pressures.

The optimum overall catalyst combination for producing a desired product may not be the one that includes the optimum catalyst for Fischer-Tropsch synthesis and the optimum catalyst for olefin isomerization, since both steps may require totally different reaction conditions to be optimized. The overall optimum combination may be one that is the optimum for Fischer-Tropsch synthesis, which defines a set of conditions, and then an olefin isomerization component that is optimized to work at the conditions needed for use with the Fischer-Tropsch catalyst. For example, the optimum conditions for Fischer-Tropsch synthesis may involve temperatures at a first temperature range, but the optimum olefin isomerization catalysts may operate best at temperatures at a different temperature range. When these "optimum" olefin isomerization catalysts are operated at temperatures in the first temperature range, they may be inefficient. Accordingly, it is preferred that the catalyst combinations include a combination that is optimum for both steps, Fischer-Tropsch synthesis and olefin isomerization, under the operating conditions imposed by the Fischer-Tropsch catalyst (satisfactory activity and relatively low methane yields.) Alternatively, the method can determine an optimum Fischer-Tropsch catalyst that operates satisfactorily under the optimum olefin isomerization conditions. Either way, it is important to test both catalyst components together, at least where both are to be combined in a single reactor using a single set of reaction conditions. However, leads for this screening of optimum catalyst combinations can come from searching the individual catalysts. This screening optionally but preferably also considers the methods of pre-treating the catalysts, alone or together.

The properties of the reaction products generated during the evaluation of the libraries for a particular chemical reaction can be measured and correlated to specific combinations of catalysts. By screening numerous combinations of catalysts, the selection of the optimal combinations is more a function of the data collection method than the "rational" basis for selecting a useful catalyst combination. Optimum combinations can be rapidly determined by directly correlating the product streams obtained with the catalyst combinations within a particular array or sub-array.

Syngas

Typically, synthesis gas contains hydrogen and carbon monoxide, and may include minor amounts of carbon dioxide and/or water. When iron-containing catalysts are used, the ratio of hydrogen/carbon monoxide over the catalyst is preferably between about 0.5 and 1.0, preferably around 0.5. When cobalt-containing catalysts are used, the ratio of hydrogen/carbon monoxide is preferably greater than 1.0, more preferably between about 1.0 and 2.0, still more preferably between about 1.0 and 1.5. A hydrogen/carbon monoxide ratio of 1.0 or less results in the formation of a relatively large proportion of oxygenated products, and for this reason should be avoided. The usage ratio is about 2.1, so commercial operation at other ratios at the catalyst would typically require an appropriate recycle of unreacted syngas.

The presence of sulfur, nitrogen, halogen, selenium, phosphorus and arsenic contaminants in the syngas is undesirable. For this reason, it is preferred to remove sulfur and other contaminants from the feed before performing the Fischer-Tropsch chemistry. Means for removing these contaminants are well known to those of skill in the art. For example, ZnO guardbeds are preferred for removing sulfur impurities. Means for removing other contaminants are well known to those of skill in the art.

Catalysts

A. Fischer-Tropsch Catalysts

In general, Fischer-Tropsch catalysts contain a Group VIII transition metal on a metal oxide support. The catalysts may also contain a noble metal promoter(s) and/or crystalline molecular sieves. Certain catalysts and conditions are known to provide chain growth probabilities that are relatively low to moderate, and the product of the reaction includes a relatively high proportion of low molecular ($C_{2-8}$) weight olefins and a relatively low proportion of high molecular weight ($C_{30}+$) waxes. Certain other catalysts and conditions are known to provide relatively high chain growth probabilities. Such catalysts are well known to those of skill in the art and can be readily obtained and/or prepared.

Catalysts operated with low chain growth probabilities

Typically, catalysts operated with an alpha value between about 0.600 and 0.700 are considered to have low chain growth probabilities. Catalysts operated with an alpha value between about 0.700 and 0.850 have moderate chain growth probabilities. Catalysts with an alpha value greater than about 0.850 have high chain growth probabilities.

Typically, catalysts operated with low chain growth probabilities are iron-containing catalysts. Iron itself can be used and, when iron oxides are formed, can be reduced with hydrogen back to iron. However, because the presence of iron fines in the product stream is not preferred, and because iron oxides (rust) decrease the surface area of the catalyst available for reaction, other iron-containing catalysts have been developed. Examples of suitable iron-containing catalysts include those described in U.S. Pat. No. 4,544,674 to Fiato et al. and Xu et al., pp. 47–53, *Chemtech* (January 1998).

The iron-containing catalysts typically include at least about 10 to about 60 weight percent iron. These catalysts can be unsupported, or promoted with a refractory metal oxide ($SiO_2$, $Al_2O_3$, etc.), alkali (K, Na, Rb) and/or Group IB metals (Cu, Ag).

Co-precipitated iron-based catalysts, including those containing cobalt, can be used. High levels of cobalt in an iron-cobalt alloy are known to produce enhanced selectivity to olefinic products, as described, for example, in *Stud. Surf. Sci. Catal.* 7, Pt/A, p. 432 (1981).

Examples of co-precipitated iron-cobalt catalysts and/or alloys include those described in U.S. Pat. Nos. 2,850,515, 2,686,195, 2,662,090, and 2,735,862; *AICHE* 1981 *Summer Nat'l Meeting Preprint No.* 408, "The Synthesis of Light Hydrocarbons from CO and $H_2$ Mixtures over Selected Metal Catalysts" ACS 173rd Symposium, Fuel Division, New Orleans, March 1977; *J. Catalysis* 1981, No. 72(1), pp. 37–50; *Adv. Chem. Ser.* 1981, 194, 573–88; *Physics Reports* (Section C of Physics Letters) 12 No. 5 (1974) pp. 335–374; UK patent application No. 2050859A; *J. Catalysis* 72, 95–110 (1981); *Gmelins Handbuch der Anorganische Chemie* 8, Auflage (1959), pg. 59; *Hydrocarbon Processing*, May 1983, pp. 88–96; and *Chem. Ing. Tech.* 49 (1977) No. 6, pp. 463–468.

Methods for producing high surface area metal oxides are described, for example, in the P. Courte and B. Delmon, *C. R. Acad. Sc. Paris*, p. 268 (May 28, 1969). Metal oxides with a high surface area are prepared by evaporating to dryness aqueous solutions of the corresponding glycolic acid, lactic acid, malic or tartaric acid metal salts. One oxide that was prepared was $CoFe_2O_4$.

Iron-cobalt spinels that contain low levels of cobalt, in an iron/cobalt atomic ratio of 7:1 to 35:1, are converted to Fischer-Tropsch catalysts upon reduction and carbiding (see, for example, U.S. Pat. No. 4,544,674 to Fiato et al.). These catalysts tend to exhibit high activity and selectivity for $C_2$–$C_6$ olefins and low methane production, and can also be included in the catalyst libraries.

The contents of each of the patents and publications referred to above are hereby incorporated by reference.

Catalysts Operated with High Chain Growth Probabilities

Typically, catalysts operated with high chain growth probabilities are cobalt and/or ruthenium-containing catalysts, although iron promoted with alkali can also have high alpha values. One suitable cobalt catalyst that can be used is described in U.S. Pat. No. 4,579,986, as satisfying the relationship:

$$(3+4R)>L/S>(0.3+0.4R),$$

wherein:

L=the total quantity of cobalt present on the catalyst, expressed as mg Co/ml catalyst;

S=the surface area of the catalyst, expressed as $m^2$/ml catalyst; and

R=the weight ratio of the quantity of cobalt deposited on the catalyst by kneading to the total quantity of cobalt present on the catalyst.

Other suitable catalysts include those described in U.S. Pat. Nos. 4,077,995, 4,039,302, 4,151,190, 4,088,671, 4,042,614 and 4,171,320. U.S. Pat. No. 4,077,995 discloses a catalyst that includes a sulfided mixture of CoO, $Al_2O_3$ and ZnO. U.S. Pat. No. 4,039,302 discloses a mixture of the oxides of Co, Al, Zn and Mo. U.S. Pat. No. 4,151,190 discloses a metal oxide or sulfide of Mo, W, Re, Ru, Ni or Pt, plus an alkali or alkaline earth metal, with Mo—K on carbon being preferred.

U.S. Pat. No. 4,088,671 discloses minimizing methane production by using a small amount of ruthenium on a cobalt catalyst. Supported ruthenium catalysts suitable for hydrocarbon synthesis via Fischer-Tropsch reactions are disclosed, for example, in U.S. Pat. Nos. 4,042,614 and 4,171,320. Any and all of these catalysts can be included in the catalyst libraries.

In general, the amount of cobalt present in the catalyst is between about 1 and about 50 weight percent of the total catalyst composition. The catalysts can also contain basic oxide promoters such as $ThO_2$, $La_2O_3$, MgO, and $TiO_2$, promoters such as $ZrO_2$, noble metals (Pt, Pd, Ru, Rh, Os, Ir), coinage metals (Cu, Ag, Au), and other transition metals such as Fe, Mn, Ni, and Re.

Catalyst Supports

The type of support used can influence methane production. Suitable metal oxide supports or matrices that can be used to minimize methane production include alumina, titania, silica, magnesium oxide, alkaline earth titanates, alkali titanates, rare earth titanates and mixtures thereof. The catalysts can include any or all of these supports, in varying ratios of weight of support to weight of catalyst.

Typically, catalysts for slurry phase or fluid bed operation have a particle size between 10 and 110 microns, preferably between 20 and 80 microns, more preferably between 25 and 65 microns, and have a density of between 0.25 and 0.9 g/cc, preferably between 0.3 and 0.75 g/cc. Catalysts for fixed bed operation typically have particle sizes between 2 mm and 10 mm.

Promoters and Noble Metals

Methane selectivity is also influenced by the choice of promoter. Alkali metal promoters are known to reduce the methane selectivities of iron catalysts. Noble metal promoters, especially ruthenium, provide superior hydrocarbon synthesis characteristics with relatively low methane production. Noble and coinage metals promote reduction of iron and cobalt oxide precursors at low temperatures, leading to increased metal dispersions in the final catalysts and, consequently, to higher conversion activities. Where another noble metal is used, platinum and palladium are generally preferred. Copper is preferred for promotion of iron due to its lower cost. Accordingly, alkali metal promoters and/or noble and coinage metals can be included with any number of catalysts in the libraries.

Manganese Salts

The tendency for olefins to be readily hydrogenated on the cobalt catalyst tends to minimize the overall yield of $C_5$+products. The presence of manganese and manganese salts in the catalyst and/or support tends to decrease the rate of olefin hydrogenation and for this reason may be preferred.

Other modifiers that minimize olefin hydrogenation without decreasing CO hydrogenation can also be used. Examples of suitable manganese-containing materials that can be used include manganese-containing zeolites, unsupported and alumina-supported manganese oxide catalysts, manganese molybdate. Examples of manganese oxide-containing catalysts and/or supports include MnO, $Al_2O_3$—MnO, $SiO_2$—MnO, MnO-carbon, Group IVB-manganese oxides, Group VB-manganese oxides, Group IA (alkali metal)-manganese oxides, Group IIA (alkaline earth metal)-manganese oxides and rare earth-manganese oxides and mixtures thereof. The preferred support is manganese oxide. Suitable manganese-containing catalysts are described, for example, in U.S. Pat. Nos. 4,206,134 and 5,162,284. When these catalysts are used in Fischer-Tropsch chemistry under certain conditions, Cu-promoted $Co_2MnO_4$ showed an increased olefin content in the products versus Cu-promoted $Co_3O_4$. U.S. Pat. No. 4,206,134 discloses using MnO-supported Ru catalysts that also show this effect. U.S. Pat. No. 4,624,968 discloses using an iron/manganese/potassium catalyst in Fischer-Tropsch synthesis. Any and all of these catalysts are suitable for inclusion in the catalyst libraries.

Catalysts in spinel form have been formed that include cobalt and manganese, in particular copper-promoted cobalt-manganese spinels with the formula $Co_{3-x}MnO_4$, where x is from about 0.5 to about 1.2, preferably from about 0.7 to about 1.0, most preferably about 1.0. The ratio of cobalt to manganese in the spinel is between about 1.5:1 and about 5:1. The amount of copper promoter in the composition is typically from about 0.1 to about 5 gram atom percent based on the total gram atoms of cobalt and manganese of the dry composition. Copper-promoted cobalt-manganese catalysts appear to be significantly more active and also better at minimizing olefin hydrogenation than analogs promoted with copper but not containing manganese, or catalysts containing manganese but not promoted with copper. Ruthenium-containing catalysts can be used with manganese oxide, other manganesecontaining oxides or mixtures of various manganese oxides as a catalyst support. These catalysts are suitable for use in the second stage Fischer-Tropsch reaction.

The disclosures of each of the patents and articles discussed above are incorporated herein by reference in their entirety.

B. Olefin Isomerization Catalysts

Any catalyst that isomerizes alpha-olefins to internal olefins or isoolefins, and that is compatible with the Fischer-Tropsch catalyst, can be used. Typically, acidic zeolites are used to isomerize alpha olefins, although double bond isomerization tends not to require strong acidity, so other solid acids may be suitable if they are stable enough to operate under the Fischer-Tropsch conditions. Ideally, the goal is to find catalysts with both sufficient activity and selectivity for heavy isoparaffins (in the diesel fuel or lube base stock ranges).

Catalysts and reaction conditions for isomerizing olefins are well known to those of skill in the art. Such catalysts and conditions are described, for example, in U.S. Pat. Nos. 5,849,975; 5,985,238; 5,523,510; 5,177,281; 5,321,194; and 5,237,120, the contents of which are hereby incorporated by reference. Specific catalysts include high Si/Al ferrierite, steamed, acid-leached ferrierite, ZSM-22, ZSM-23, ZSM-35, surface deactivated ZSM-5, ZSM-11, ZSM-22, ZSM-23, ZSM-35, ZSM-38 and ZSM-48.

Zeolites

Catalysts useful for isomerizing alpha olefins typically include one or more zeolites and/or non-zeolitic molecular sieves. Those zeolites that are relatively acidic tend to be more efficient than those that are relatively less acidic.

The zeolites and/or molecular sieves are preferably small and/or intermediate pore size, although zeolites with large pore sizes can be included in the catalyst libraries. For example, the zeolites in the patents listed above are 10-ring zeolites, with small-to-intermediate pore sizes. Examples of these catalysts, any and all of which can be included in the catalyst libraries, are described, for example, in U.S. Pat. Nos. 3,546,102; 3,574,092; 3,679,575; 4,018,711; 4,104,320; 4,347,394; 4,370,224; 4,417,083; 4,434,311; 4,447,316 and 5,559,068. Zeolite-containing catalysts, for example the zeolite mordenite, ZSM-type zeolites, zeolite L, Faujasites X and Y, and the zeolite omega are preferably included into the catalyst libraries. L-zeolites and zeolites having an L-zeolite-type channel structure and size, such as ECR-2, which is described in U.S. Pat. No. 4,552,731, and ECR-31, which is described in U.S. Pat. No. 5,624,657 (Vaughan) are also preferably included in the libraries.

The composition of type L-zeolite expressed in terms of mole ratios of oxides, may be represented by the following formula:

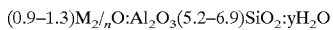

$$(0.9-1.3)M_2/_nO:Al_2O_3(5.2-6.9)SiO_2:yH_2O$$

In the above, formula M represents a cation, n represents the valence of M, and y may be any value from 0 to about 9. Zeolite L, its X-ray diffraction pattern, its properties and method for its preparation are described in detail in, for example, U.S. Pat. No. 3,216,789, the contents of which are hereby incorporated by reference. The actual formula may vary without changing the crystalline structure. For example, the mole ratio of silicon to aluminum (Si/Al) may vary from 1.0 to 3.5.

Examples of useful large pore zeolites include ZSM-3, ZSM-4, ZSM-10, ZSM-12, ZSM-20, zeolite beta, zeolite omega, zeolite L, zeolite X, zeolite Y, REY, USY, RE-USY, mordenite, LZ-210, LZ-210-M, LZ-210-T, LZ-210-A, SSZ-24, SSZ-26, SSZ-31, SSZ-33, SSZ-35, SSZ-37, SSZ-41, SSZ-42, SSZ-44 and MCM-58, any and all of which are preferably incorporated into the libraries. ZSM-3 is described in U.S. Pat. No. 3,415,736. ZSM-4 is described in UK Application No. 1,117,568. ZSM-10 is described in U.S. Pat. No. 3,692,470. ZSM-12 is described in U.S. Pat. No. 3,832,449. ZSM-20 is described in U.S. Pat. No. 3,972,983. Zeolite beta is described in U.S. Pat. No. Re. 28,341 (of original U.S. Pat. No. 3,308,069). Zeolite omega is described in U.S. Pat. No. 4,241,036. Zeolite L is described in U.S. Pat. No. 3,216,789. Zeolite X is described in U.S. Pat. No. 2,882,244. Zeolite Y is described in U.S. Pat. No. 3,130,007. LZ-210, LZ-210M, LZ-210-T, LZ-210-A and mixtures thereof are described in U.S. Pat. No. 4,534,853. SSZ-24 is described in U.S. Pat. No. 4,834,977. SSZ-26 is described in U.S. Pat. No. 4,910,006. SSZ-31 is described in U.S. Pat. No. 5,106,801. SSZ-33 is described in U.S. Pat. No. 4,963,337. SSZ-35 is described in U.S. Pat. No. 5,316,753. SSZ-37 is described in U.S. Pat. No. 5,254,514. SSZ-41 is described in U.S. Pat. No. 5,591,421. SSZ-42 is described in U.S. Ser. No. 08/199,040. SSZ-44 is described in U.S. Pat. No. 5,580,540. MCM-58 is described in U.S. Pat. No. 5,437,855.

Examples of useful intermediate pore size zeolites include ZSM-5, ZSM-11, ZSM-22, ZSM-23, ZSM-35; ZSM-48, ZSM-57, SUZ-4, SSZ-23; SSZ-25; SSZ-28, SSZ-32, and SSZ-36. ZSM-5 is described in U.S. Pat. No. Re. 29,948 (of original U.S. Pat. No. 3,702,886). ZSM-11 is described in U.S. Pat. No. 3,709,979. ZSM-22 is described in U.S. Pat.

No. 4,556,477. ZSM-23 is described in U.S. Pat. No. 4,076,842. ZSM-35 is described in U.S. Pat. No. 4,016,245. ZSM-48 is described in U.S. Pat. No. 4,585,747. SUZ-4 is described in EP Application No. 353,915. SSZ-23 is described in U.S. Pat. No. 4,859,422. SSZ-25 is described in U.S. Pat. Nos. 4,827,667 and 5,202,014. SSZ-28 is described in U.S. Pat. No. 5,200,377. SSZ-32 is described in U.S. Pat. No. 5,053,373. The entire contents of all these patents and patent applications are incorporated herein by reference, and any and all of the catalysts described therein can be incorporated into the catalyst libraries.

The isomerization of alpha olefins is believed to involve an interaction with a relatively acidic catalyst component. Bifunctional catalysts with an acid and a metal function tend to be relatively acidic and are advantageously included in the catalyst libraries. For example, when acidic crystalline aluminosilicate catalysts are used in intimate mixture with Fischer-Tropsch catalysts, isomerization tends to be observed.

The term "non-acidic" is understood by those skilled in this area of art, particularly by the contrast between monofunctional (non-acidic) reforming catalysts and bifunctional (acidic) reforming catalysts.

The entire contents of all the above-cited patents are incorporated herein by reference, and any and all of the zeolites described therein can be included in the catalyst libraries.

Carriers

Any of the catalysts described above and combinations thereof may be formed in any conventional manner, such as tableting, pelleting, or supporting the active catalyst material on a carrier. The carrier is preferably inert and may include silica, alumina, Alundum, clay, alumina-silica, silicon carbide, zeolite, and the like. The catalysts can be incorporated into solid particles in which the catalyst is present in an amount and with sufficient exposed surface effective to promote the desired conversion.

In one aspect, the solid particles comprise a catalytically effective amount of the catalyst and at least one matrix material, preferably selected from the group consisting of binder materials, filler materials, and mixtures thereof to provide a desired property or properties, e.g., desired catalyst dilution, mechanical strength, and the like to the solid particles. Filler and binder materials include, for example, synthetic and naturally occurring substances such as metal oxides, clays, silicas, aluminas, silica-aluminas, silica-magnesias, silica-zirconias, silica-thorias, silica-berylias, silica-titanias, silica-alumina-thorias, silica-alumina-zirconias, aluminophosphates, mixtures of these and the like. If matrix materials, e.g., binder and/or filler materials, are included in the catalyst composition, the catalysts typically comprise about 1 to 99%, more typically about 5 to about 90%, by weight of the total composition.

The preparation of solid particles comprising catalyst and matrix materials is conventional and well known in the art and, therefore, need not be discussed in detail herein.

Arrays

Libraries of catalysts can be prepared and evaluated using the devices and methods described herein. The first and second catalyst systems are preferably arranged (preferably in the reaction vessels) in the form of arrays. The catalysts can be, but need not be, mixed directly in the reaction vessels. Alternatively, they can be mixed ahead of time. In a less preferred embodiment, a single catalyst of a first type (a Fischer-Tropsch or olefin isomerization catalyst) is evaluated with a plurality of a second type of catalyst, and then subsequent catalysts of the first type can be evaluated with a plurality of the second type of catalyst, with the process repeated as desired. Preferably, the preparation of the catalyst libraries and/or the transfer of the catalysts to the reaction vessels is automated.

Preferably, the process involves generating a matrix including a first catalyst system and a second catalyst system. The synthesis is performed in a device that can handle the temperature and pressure requirements, as well as being able to handle a plurality of catalyst combinations (preferably more than 5 catalyst combinations at a time, more preferably greater than 20 catalyst combinations at a time, and, more preferably more than about 50 catalyst combinations at a time) and the product stream from the various reactions is then evaluated. Reaction vessels useful for conducting reactions under relatively high temperatures and pressures are well known to those of skill in the art.

The identity of the catalyst system in each reaction vessel or in each position in a reaction vessel can be stored in a computerized device or identified via a bar code or other similar identifying means. The products of the reaction can be readily identified, for example by gas chromatography (GC), a combination of gas chromatography and mass spectrometry (GC/MS), infrared heat emissions or infrared species analysis, or UV spectral analysis. To avoid contaminating the columns in chromatographic devices, it may be desirable to filter a representative sample of the product stream before it is placed on the column, for example using an in-line filter or an in-line solid phase extraction (SPE) column.

Reactors suitable for conducting chemistry

As used herein, a reaction vessel is any suitable container that can hold a plurality of combinations of catalyst systems, that can contain from about 200 mg to about 100 g, preferably, from about 1 mg to about 10 g of each catalyst combination, and that can handle the reaction conditions necessary for converting syngas to product streams including hydrocarbons in the distillate fuel and/or lube base oil ranges, for example conditions of increased pressure and temperature.

Any reaction vessel that is capable of being used to conduct a plurality of simultaneous reactions using gas phase reactants and solid catalysts under conditions of elevated temperature and pressure can be used. Such reaction vessels are well known to those of skill in the art. Examples of suitable devices include those described, for example, in U.S. Pat. No. 5,980,839 to Bier et al., U.S. Pat. No. 6,036,923 to Laugharn, Jr. et al., U.S. Pat. No. 6,030,917 to Weinberg et al., U.S. Pat. No. 6,001,311 to Brennan, the contents of each of which are hereby incorporated by reference.

The reaction vessel can contain multiple sample vessels, in parallel or in series, to perform combinatorial or sequential operations, respectively. The reactor can include a reaction region that includes a plurality of individual reaction cavities, each of which can have a port adapted to supply or remove reagents, solvents, gases and/or vacuum suction to the cavity. There can be a mixing region disposed adjacent to the reaction region, such that the reaction cavities open into the mixing region. The reaction cavities are preferably well enough isolated from one another and with sufficient heat control that the heat released during the reaction does not cause excessive temperature rises in any of the adjacent cavities.

The vessel can be constructed from a variety of materials, depending on the pressure and temperature requirements of the reaction, examples of which can include certain plastics, glass and certain metals such as stainless steel.

The scale of the synthetic reactions is preferably in the range of greater than about 200 mg, more preferably between one g and 100 g, although the scale can be modified depending on the amount of compound necessary for the particular application. Depending on the reaction vessel, it may be difficult to correlate the products obtained at smaller reaction scales with those obtained at commercial scale due to anticipated differences in heat transfer kinetics on scale-up. The reactions are typically performed under conditions of relatively high temperature and/or pressure. Following the reactions, the products can be characterized using a variety of means, for example, GC, GC/MS, HPLC and the like.

Robotic arms and multi-pipet devices can be used to add appropriate catalysts to the appropriate locations in the reaction vessel. When appropriate, the chemistry can be performed under varying conditions of temperature, pressure, flow rate and the like. When elevated temperatures and pressures are required, devices capable of handling elevated temperatures and pressures, particularly for use in combinatorial chemistry, are used.

In one embodiment, the reactions are carried out via computer control. The identity of each of the catalysts can be stored in a computer in a "memory map" or other means for correlating the data regarding the chemical reactions to the catalyst combinations in the reaction vessels. Alternatively, the chemistry can be performed manually and the information stored, for example on a computer.

Those of skill in the art can readily determine appropriate sets of reactions and reaction conditions to generate and/or evaluate the libraries of interest.

Operating Conditions

Examples of conditions for performing Fischer-Tropsch type reactions are well known to those of skill in the art. Suitable conditions are described, for example, in U.S. Pat. Nos. 4,704,487, 4,507,517, 4,599,474, 4,704,493, 4,709,108, 4,734,537, 4,814,533, 4,814,534 and 4,814,538, the contents of each of which are hereby incorporated by reference in their entirety.

The Fischer-Tropsch reaction using iron-containing catalysts is typically conducted at temperatures between about 270° C. and 300° C., at a pressure of between about 1 and 20 ATM, in a slurry reactor or a fluidized bed reactor. Typical synthesis gas linear velocity ranges in the reactor are between about 2 and 40 cm per sec., preferably between about 6 and 10 cm per sec.

The Fischer-Tropsch reaction using cobalt-containing catalysts is typically conducted in either a fixed bed reactor or a slurry reactor, where slurry reactors are preferred. The operating temperature of the fixed bed reactor is between about 200° C. and 225 ° C., and the operating temperature of the slurry reactor is between about 225° C. and 250° C., with a temperature around 240° C. preferred. Typical synthesis gas linear velocity ranges in the reactor are from about 2 to 40 cm per sec., preferably from about 6 to 10 cm per sec. The pressure is preferably between about 1 and 30 ATM, with pressures between 20 and 30 ATM being particularly preferred. Above about 30 ATM, carbonyls may be formed and, therefore, pressures significantly about 30 ATM are not preferred. Further, the rate of reaction tends to increase with increased pressure, but tends to level off due to hydrodynamic problems at around 30 ATM.

The catalyst space velocities are typically between about 100 and 10,000 cc/g/h, preferably between about 300 and 3,000 cc/g/h, for either set of reaction conditions.

As discussed above, slurry reactors can be preferred for either set of conditions. Bubble column slurry reactors can be particularly preferred. Details regarding bubble column slurry reactors can be found, for example, in Y. T. Shah et al., "Design Parameters Estimations for Bubble Column Reactors," *AIChE Journal,* 28 No. 3 pp. 353–379 (May 1982); Ramachandran et al., *Bubble Column Slurry Reactor, Three-Phase Catalytic Reactors,* Chapter 10, pp. 308–332 Gordon and Broch Science Publishers (1983); Deckwer et al., "Modeling the Fischer-Tropsch Synthesis in the Slurry Phase," *Ind. Eng. Chem. Process Des. Dev.* v 21, No. 2, pp. 231–241 (1982); Kölbel et al., "The Fischer-Tropsch Synthesis in the Liquid Phase," *Catal. Rev.-Sci. Eng.,* v. 21(n), pp. 225–274 (1980); and U.S. Pat. No. 5,348,982, the contents of each of which are hereby incorporated by reference in their entirety.

Since the catalyst metal may be present in the catalyst in the form of an oxide, the catalyst may be reduced with hydrogen prior to contact with the slurry liquid, or, in the case of iron catalysts, carbided with CO. The starting slurry liquid is typically a heavy hydrocarbon that is viscous enough to keep the catalyst particles suspended (typically a viscosity between 4 and 100 centistokes at 100° C.) and a low enough volatility to avoid vaporization during operation (typically an initial boiling point range of between about 350° C. and 550° C.). The slurry liquid is preferably essentially free of contaminants such as sulfur, phosphorous or chlorine compounds. Initially, it may be desirable to use a synthetic hydrocarbon fluid such as a synthetic olefin oligomer as the slurry fluid.

The slurry typically has a catalyst concentration of between about 2 and 40 percent catalyst, based on the total weight of the catalyst, i.e., metal plus support.

Although the stages described herein are described in terms of a Fischer-Tropsch reaction, these stages can optionally be performed using various modifications of the literal Fischer-Tropsch process where hydrogen (or water) and carbon monoxide (or carbon dioxide) are converted to hydrocarbons (e.g., paraffins, ethers, etc.). Thus, the term Fischer-Tropsch type product or process is intended to apply to Fischer-Tropsch processes and products and the various modifications thereof and the products thereof. For example, the term is intended to apply to the Kolbel-Engelhardt process.

When performed commercially, the $CO_2$ product of the Kolbel-Engelhardt process can be returned to the syngas generator and combined with methane (and some air) to form additional syngas.

The products from Fischer-Tropsch reactions generally include a gaseous reaction product and a liquid reaction product. The gaseous reaction product includes hydrocarbons boiling below about 650° F. (e.g., tail gases through middle distillates). The liquid reaction product (the condensate fraction) includes hydrocarbons boiling above about 650° F. (e.g., vacuum gas oil through heavy paraffins).

Commercially, the minus 650° F. product is typically separated into a tail gas fraction and a condensate fraction, i.e., about $C_5$ to $C_{20}$ normal paraffins and higher boiling hydrocarbons, using, for example, a high pressure and/or lower temperature vapor-liquid separator or low pressure separators or a combination of separators.

The fraction boiling above about 650° F. (the condensate fraction) is typically separated into a wax fraction boiling in the range of about 650° F.–1200° F. after removing particulate catalyst fines and one or more fractions boiling above about 1200° F. The wax fraction primarily contains $C_{20}$ to $C_{50}$ linear paraffins with relatively small amounts of higher boiling branched paraffins. Commercially, the separation is typically effected by fractional distillation. However, for purposes of evaluating combinatorial libraries, the separation is preferably effected by gas chromatography. The amounts of each component can be determined and the information regarding the effectiveness of each set of reaction conditions can be stored.

Method Steps

The method steps in the preferred embodiment of the present invention involve:

a) preparing a logical array of a plurality of catalyst combinations in one or more reaction vessels, where the array includes one or more catalysts from a first catalyst system (Fischer-Tropsch catalysts), and one or more catalysts from a second catalyst system (olefin isomerization catalysts), b) optionally but preferably pretreating and activating them in a reducing and/or carbiding environment, c) introducing syngas to the reaction vessel(s) under conditions that convert syngas to product streams, preferably including hydrocarbons in the distillate fuel and/or lube base oil ranges, d) analyzing the contents of the product streams, and e) optionally storing information regarding the identity of the catalysts and/or the contents of the product streams in a relational database.

It is preferred that the catalyst combinations (or composites) be evaluated in a single reactor, although the catalysts can be evaluated in separate reactors.

In one embodiment, the reaction conditions (syngas composition, temperature and pressure) should be kept reasonably constant while evaluating the entire library, and then the reaction conditions are modified and the library is re-evaluated with the modified reaction conditions. In another embodiment, all of the significant variables are varied at once. In either embodiment, it may be easier and faster experimentally to give all samples a common pre-treatment, modifying the pre-treatments as desired to increase the size of the catalyst library. Accordingly, steps a–e can be repeated one or more times, with varying reaction conditions (for example, changes in syngas composition, temperatures and/or pressures, and, optionally, catalyst pre-treatment steps) to obtain additional information.

The devices and processes described herein can be used for the rapid determination and optimization of desired catalyst activity for producing a given desired product stream. An array of catalyst systems can be screened and the optimum candidates for providing a desired product stream identified. This process can be repeated as desired to provide information regarding the catalyst systems of interest and the selection can be accelerated by the rapid modular synthesis of arrays for use in testing.

Combinations of catalysts that appear to provide desired product streams can optionally be scaled up (for example, in a lead optimization step) to obtain additional data and to fine-tune the process. For example, once ideal catalyst combinations are identified in a lead generation step, the reaction conditions (syngas composition, temperature and pressure) can be optimized in a lead optimization step.

The devices and processes described herein can be used for the logical and rapid analysis of synthetic results for various properties, including cetane and/or octane values, degree of isomerization, olefin concentration, and the like. One can determine the efficacy of a synthetic strategy by testing a series of loci within any given array. Accordingly, the general usefulness of various catalyst combinations for providing a desired product stream can be determined.

The devices and methods described herein provide for the complete control of the analysis of entire libraries of catalyst combinations.

Products

In any Fischer-Tropsch synthesis, methane will invariably be produced to some degree. For purposes of the combinatorial chemistry described herein, it may be of interest to determine how much methane is produced, since methane production is undesirable. However, when scaled up to commercial scale, any methane produced during the reaction may be recovered, converted to synthesis gas, and recycled.

The products can include olefins such as ethylene, iso-paraffins, and combinations thereof, and preferably include iso-paraffins in the distillate fuel and/or lube base stock ranges and, more preferably, iso-paraffins in the jet or diesel range.

Branching may be advantageous in a number of end-uses, particularly when increased octane values (when the compositions are used as fuels) or decreased pour points are desired. The degree of isomerization is preferably greater than 1, and more preferably greater than 3 moles of isoparaffin per mole of n-paraffin. When used in a diesel fuel composition, the products preferably have a cetane number of at least 60. When used in a lube oil composition, the products preferably have a viscosity index of at least 80, more preferably at least 100 and most preferably at least 110. The ideal lube base stock is suitable for use in lube oil compositions.

Commercially, higher molecular weight products, for example waxes, can either be isolated and used directly, or can be reacted to form lower molecular weight products, as desired. For example, high molecular weight products can be hydrocracked to provide lower molecular weight products, increasing the yield of liquid combustible fuels. Hydrocracking refers to a catalytic process, usually carried out in the presence of free hydrogen, in which the cracking of the larger hydrocarbon molecules is a primary purpose of the operation. Catalysts used in carrying out hydrocracking operations are well known in the art, and it should not be necessary to describe them in detail here. See, for example, U.S. Pat. Nos. 4,347,121 and 4,810,357 for general descriptions of hydrotreating, hydrocracking, and typical catalysts used in each process. The product from the hydrocracking can be subject to distillation and/or catalytic isomerization to provide lube oils, diesel fuel, and the like. While it is preferred that such products are not produced in large quantities in the reactions described herein, it may be useful to quantify the amount of such compounds, as well as the identity of the catalysts and conditions that provided them.

Analytical Chemistry

The products of the reactions can be analyzed in a high throughput manner, for example using HPLC, GC, GC/MS and/or other analytical methods. The products can be assayed for various properties, including octane and/or cetane values, degree of isomerization, olefin concentration, and the like.

Any device that can take samples from the individual positions in the reaction vessels and analyze the resulting compounds can be used. Preferably, the device is a chromatographic device, such as an analytical or preparative scale HPLC, GC or GC/MS, although other devices can be envisioned, depending on the chemistry performed. Since the product stream does not likely include UV-active compounds, the analytical equipment preferably includes an ELSD detector or other detector that is not dependent on Uv absorption to detect a compound eluting from the column. Preferably, the analytical techniques are set up to handle a plurality of simultaneous analyses or otherwise optimized to handle the plurality of samples.

After the chemical reactions take place, the contents of the reaction vessels (or a representative sample thereof) can be individually transferred to an analytical device. Those of skill in the art can readily optimize the reactions by varying various process conditions, for example reagent composition, temperature, pressure, flow rate and the like.

Particularly when iso-paraffin concentration is evaluated using the library, a combination of GC and MS is used. Isomers tend to have the same MS peaks, but elute at different times from the columns, and this technique allows rapid determination of the product stream.

Conditions are known in the art for determining the octane or cetane values based on known GC data, when a GC is performed on a representative sample of the product stream. These techniques may be particularly useful in evaluating the libraries for useful catalyst combinations for preparing products with desirable properties.

Database

Data regarding the catalyst combinations, reaction conditions and product streams can be stored in a relational database. The database can be used to find optimum catalyst combinations for a desired product stream, and can be particularly useful when the desired product stream varies depending on market factors. When the product requirements change, appropriate catalyst combinations and/or reaction conditions can be selected to prepare the desired product.

The device preferably includes a computer system capable of storing information regarding the identity of the catalysts and the product streams obtained, particularly when a plurality of different reaction conditions are used. Software for managing the data is stored on the computer. Relational database software can be used to correlate the identity of the catalysts, the reaction conditions (for example, reagent composition, temperature and pressure) and the analytical data from each product stream. Numerous commercially available relational database software programs are available, for example from Oracle, Tripos, MDL, Oxford Molecular ("Chemical Design"), IDBS ("Activity Base"), and other software vendors.

Relational database software is a preferred type of software for managing the data obtained during the processes described herein. However, any software that is able to create a "memory map" of the catalysts in the reaction vessels and correlate that information with the information obtained from the chemical reactions can be used. This type of software is well known to those of skill in the art.

Library Design

Software for the design of test libraries can be used to design the original catalyst test libraries based on input from literature and previous experimental programs. This software can be used to efficiently design test libraries that cover the desired experimental space and utilize statistical experimental design methods.

Other software can be used to analyze the data from experiments and correlate that data with the structure of the catalysts and/or catalyst treatment conditions and/or reaction conditions. Such correlations are often referred to as QSAR software (Quantitative Structure Activity Relations). Such QSAR can then be used by the software to design subsequent catalyst test libraries for further screening. The use of such QSAR programs can add to the efficiency of screening. As more data is collected, these QSAR programs can become more efficient at developing catalyst libraries with increased probability for finding desirable catalysts.

We claim:

1. A method for discovering optimum catalyst systems for the conversion of syngas to higher molecular weight products via Fischer-Tropsch synthesis, comprising:
   a) preparing a first library of catalysts comprising Fischer-Tropsch catalysts,
   b) preparing a second library of olefin isomerization catalysts,
   c) preparing a plurality of combinations of catalysts from the first and second libraries in a logical manner, and
   d) reacting syngas with the combinations of catalysts under appropriate reaction conditions to form a plurality of reaction products.

2. The method of claim 1, wherein the library of catalysts includes catalysts of similar composition but with varying catalyst pre-treatments.

3. The method of claim 1, further comprising analyzing the reaction products.

4. The method of claim 1, further comprising storing information regarding the identity of the catalysts in the plurality of combinations of catalysts in a database.

5. The method of claim 3, further comprising storing information regarding the analysis of the reaction products in a database.

6. The method of claim 1, wherein the combinations of catalysts are arranged in a logical array.

7. The method of claim 1, wherein step d) is repeated at least one time using different reaction conditions.

8. The process of claim 7, wherein the reaction conditions that are varied are selected from the group consisting of temperature, pressure, syngas composition, and flow rate.

9. The process of claim 2, wherein the catalyst pre-treatment conditions that are varied are selected from the group consisting of the time and temperature of catalyst washing, heating rate, hold time, hold temperature, relative humidity during drying or calcining; hydrogen content and total pressure during catalyst reduction, CO partial pressure during activation in CO; treatment with citrate, alcohols, or metal hydrides, modification of catalyst acidity, vapor deposition of Si or Al species and steaming.

10. The method of claim 1, wherein at least one of the catalysts is a zeolite.

11. The method of claim 10, wherein at least one of the catalysts is an intermediate pore size zeolite.

12. The method of claim 1, wherein the product stream includes iso-paraffins in the jet fuel range.

13. The method of claim 1, wherein the product stream includes iso-paraffins in the diesel fuel range.

14. The method of claim 1, wherein the product stream includes iso-paraffins in the lube base oil range.

15. A method for rapidly determining an appropriate set of reaction conditions and catalyst combinations to form a desired product via conversion of syngas to hydrocarbons comprising:
   a) preparing a first library of Fischer-Tropsch catalysts,
   b) preparing a second library of olefin isomerization catalysts,
   c) preparing a plurality of combinations of catalysts from the first and second libraries in a logical manner, and
   d) reacting syngas with the combinations of catalysts under a plurality of reaction conditions to form a plurality of reaction products, wherein each set of reaction conditions is applied to all or substantially all of the catalyst combinations, e) storing information regarding the products of the reactions in a database, and f) identifying an appropriate set of reaction conditions and catalyst combinations to produce the desired product.

16. A method for rapidly determining an appropriate set of reaction conditions and catalysts to form a desired product comprising:

a) preparing a library of catalysts that are active at both Fischer-Tropsch synthesis and olefin isomerization, b) reacting syngas with the catalysts under a plurality of reaction conditions to form a plurality of reaction products, wherein each set of reaction conditions is applied to all or substantially all of the catalysts, c) storing information regarding the products of the reactions in a database, and d) identifying an appropriate set of reaction conditions and catalysts to produce the desired product.

* * * * *